(12) United States Patent
Zhang et al.

(10) Patent No.: US 6,891,989 B2
(45) Date of Patent: May 10, 2005

(54) OPTICAL SWITCH SYSTEMS USING WAVEGUIDE GRATING-BASED WAVELENGTH SELECTIVE SWITCH MODULES

(75) Inventors: Jianjun Zhang, Cupertino, CA (US); Peiching Ling, San Jose, CA (US); Jinliang Chen, Saratoga, CA (US); Ming Xu, San Jose, CA (US)

(73) Assignee: Integrated Optics Communications Corporation, Sunnyvale, CA (US)

( * ) Notice: Subject to any disclaimer, the term of this patent is extended or adjusted under 35 U.S.C. 154(b) by 165 days.

(21) Appl. No.: 10/274,508

(22) Filed: Oct. 15, 2002

(65) Prior Publication Data

US 2003/0108275 A1 Jun. 12, 2003

Related U.S. Application Data
(60) Provisional application No. 60/373,803, filed on Apr. 19, 2002, provisional application No. 60/346,567, filed on Jan. 8, 2002, provisional application No. 60/346,066, filed on Jan. 3, 2002, and provisional application No. 60/348,927, filed on Oct. 22, 2001.

(51) Int. Cl.[7] .............................................. G02B 6/26
(52) U.S. Cl. .............................. 385/16; 385/17; 385/37
(58) Field of Search ............................... 385/16–18, 37

(56) References Cited

U.S. PATENT DOCUMENTS

| | | | |
|---|---|---|---|
| 3,918,794 A | | 11/1975 | Milton |
| 4,013,000 A | | 3/1977 | Kogelnik |
| 4,240,693 A | | 12/1980 | Johnson et al. |
| 5,040,864 A | * | 8/1991 | Hong ............................ 385/16 |
| 5,255,332 A | * | 10/1993 | Welch et al. .................. 385/17 |
| 5,422,611 A | | 6/1995 | Kashima et al. |
| 5,444,802 A | | 8/1995 | Shibata et al. |
| 5,652,817 A | | 7/1997 | Brinkman et al. |
| 5,701,371 A | * | 12/1997 | Ishida .......................... 385/17 |
| 5,703,710 A | * | 12/1997 | Brinkman et al. .......... 359/283 |

(Continued)

FOREIGN PATENT DOCUMENTS

| | | |
|---|---|---|
| JP | 2151842 | 6/1990 |
| JP | 2001324734 | 11/2001 |
| JP | 2003195200 | 7/2003 |
| WO | WO 02/23244 | 3/2002 |

OTHER PUBLICATIONS

Harry J. R. Dutton, "Characteristics on In–Fibre Bragg Gratings", Understanding Optical Communications, Jan. 15, 1999, pp. 268–271, Prentice Hall PTR, Upper Saddle River, New Jersey, US.

B.J.Eggleton, et al., "Integrated Tunable Fiber Gratings for Dispersion Management in High–Bit Rate Systems", Journal of Lightwave Technology, Oct. 2000, pp. 1418–1432, vol. 18, No. 10, IEEE, New York, NY, US.

Mark Barratt, "Dispersion Management for the Next Generation Optical Network", Communications Design Conference, Oct. 2001, pp. 1–4, LaserComm Inc., Plano TX, US.

*Primary Examiner*—Ellen E. Kim
(74) *Attorney, Agent, or Firm*—Perkins Coie LLP

(57) ABSTRACT

The present invention discloses methods and apparatus for constructing optical switch systems, in which any input optical signals can be routed to any output ports. The methods and apparatus provide advantages of configuration flexibility, modular construction, constant signal loss, and minimal numbers of switch units required. The switch systems comprise M×N switch modules. The switch module in turn comprises a two-dimensional waveguide array and a number of waveguide grating-based wavelength selective switches. With the capability of wavelength-selective routing provided by the switch modules, the optical switch systems requires a relatively small amount of switch units to extend into a very-large-scale switch system.

5 Claims, 9 Drawing Sheets

U.S. PATENT DOCUMENTS

| | | |
|---|---|---|
| 5,778,119 A | 7/1998 | Farries |
| 5,802,222 A | 9/1998 | Rasch et al. |
| 5,805,751 A | 9/1998 | Kewitsch et al. |
| 5,835,458 A * | 11/1998 | Bischel et al. ............ 369/44.12 |
| 5,862,276 A | 1/1999 | Karras |
| 5,875,272 A | 2/1999 | Kewitsch et al. |
| 5,915,051 A | 6/1999 | Damask et al. |
| 6,061,484 A | 5/2000 | Jones et al. |
| 6,289,699 B1 | 9/2001 | Kewitsch et al. |
| 6,298,180 B1 | 10/2001 | Ho |
| 6,356,679 B1 | 3/2002 | Kapany |
| 6,360,038 B1 | 3/2002 | Grubsky |
| 6,389,189 B1 | 5/2002 | Edwards et al. |
| 6,404,943 B1 | 6/2002 | Wang |
| 6,501,874 B1 | 12/2002 | Frolov et al. |
| 6,522,795 B1 | 2/2003 | Jordan et al. |
| 6,546,163 B2 * | 4/2003 | Thackara ..................... 385/18 |
| 6,567,573 B1 | 5/2003 | Domash et al. |
| 6,658,176 B2 | 12/2003 | Amantea |
| 2001/0046352 A1 | 11/2001 | Ohta et al. |
| 2002/0024717 A1 | 2/2002 | Nakamura |
| 2002/0054727 A1 * | 5/2002 | Song ........................... 385/16 |
| 2002/0063944 A1 | 5/2002 | Kim et al. |
| 2002/0150330 A1 | 10/2002 | Kopp et al. |
| 2003/0194179 A1 | 10/2003 | Rumpf et al. |
| 2003/0219197 A1 | 11/2003 | Kawamoto |

* cited by examiner

OPTICAL SWITCH SYSTEMS USING WAVEGUIDE GRATING-BASED WAVELENGTH SELECTIVE SWITCH MODULES

CROSS-REFERENCE TO RELATED APPLICATION

Priority is hereby claimed under 35 U.S.C. § 120 to U.S. Provisional Patent Application Ser. No. 60/348,927 filed Oct. 22, 2001, U.S. Provisional Patent Application Ser. No. 60/346,066 filed Jan. 3, 2002, U.S. Provisional Patent Application No. 60/346,567 filed Jan. 8, 2002, U.S. Provisional Patent Application Ser. No. 60/373,803 filed Apr. 19, 2002, U.S. patent application Ser. No. 10/104,273 filed Mar. 22, 2002, U.S. patent application Ser. No. 10/177,632 filed Jun. 19, 2002, U.S. patent application Ser. No. 10/188,955, filed Jul. 3, 2002, U.S. patent application Ser. No. 10/190,018, filed Jul. 5, 2002, and U.S. patent application Ser. No. 10/202,054, filed Jul. 23, 2002, each of which is hereby incorporated by reference in its entirety.

BACKGROUND OF THE INVENTION

1. Field of the Invention

This invention relates generally to optical switching systems, and more particularly, to a method and apparatus for routing input signals into all possible output combinations by using waveguide grating-based wavelength selective switch modules.

2. Description of the Related Art

Current optical switching and signal transmission systems are limited to optical switching of an entire spectrum without wavelength differentiation or selection. Due to the lack of wavelength selection, an optical switch must frequently operate in conjunction with a demultiplexer and multiplexer to achieve routing of optical signals having different wavelengths to different ports. This requirement leads to more complicated system configurations, higher manufacture and maintenance costs, and lower system reliability. For this reason, even though optical switches are advantageous because the optical signals are switched entirely in the optical domain without converting them into the electrical domain, the cost and size of such optical switches can be prohibitive for many applications.

Thus, there is a need to further improve optical switches, since they are considered critical enabling technology for optical-fiber networks. In the wavelength division multiplex (WDM) networks of the past, the adding, dropping or cross-connecting of individual wavelengths has involved conversion of the signal into the electrical domain. Development of all-optical switches for applications ranging from add-drop functionality to large-scale cross-connects is key to efficient optical networking systems. However, with current technical limitations, an all fiber network implemented with optical switches are still quite expensive.

The primary optical switching technologies being developed today are: micro electromechanical systems (MEMS), liquid crystals, thermal-optics, holograms, acousto-optic, etc. Among all these optical switching technologies, MEMS is emerging to be the most promising technology, thanks to its potential for economical mass production, as well as its reliability in a wide range of applications. The other technologies are still in the experimental stage and will require years of development to become reliable enough for commercial applications.

There are two types of optical MEMS switch architectures under development, or commercially available: mechanical and micro-fluidic. Mechanical-type MEMS-based switches use arrays of miniaturized mirrors fabricated on a single chip. The optical signal is reflected off this tiny mirror in order to change the transmission channel. Micro-fluidic-type MEMS-based switches, on the other hand, have no moving mirrors. Rather, they rely on the movement of bubbles in micro-machined channels.

Mechanical-type MEMS-based switches can be further classified into two categories according to mirror movement: two-dimensional (2-D) switches and three-dimensional (3-D) switches. In 2-D switches, the mirrors are only able to execute a two-position operation—that is, the mirrors can move either up and down or side by side. In 3-D switches, the mirrors can assume a variety of positions by swiveling along multiple axes. These products (2-D switches or 3-D switches) are able to offer such benefits as excellent optical performance, minimal cross-talk, and the promise of improved integration, scalability, and reliability. However, in these switches, light travels through free space, which causes unbalanced power loss. Further, in order to steer each mirror, multiple electrodes need to be connected to each mirror, which increases manufacturing complexity, particularly for large-scale mechanical-type MEMS-based switches. Finally, alignment and packaging are problematical for large-scale switches.

While the above-mentioned micro-mirror-based approach is widely pursued by many manufacturers to build their MEMS-based optical switches, Agilent Technology, Inc. has developed micro-fluidic-type, MEMS-based switches by combining its micro-fluidics and ink-jet printing technology. In these switches, an index-matching fluid is used to select and switch wavelengths. This fluid enables transmission in a first, normal condition. To redirect light from an input to another output, a thermal ink-jet element creates a bubble in the fluid in a trench located at the intersection between the input wave-guide and the desired output wave-guide, reflecting the light by total internal reflection. The advantages of these switches are that they have no moving mechanical parts and are polarization independent. However, these types of switches have not been proven to be completely reliable. Further, these switches often result in insertion loss for large-scale switches.

A common drawback of both of these two types of MEMS-based switches is the requirement to work with external de-multiplexing and re-multiplexing systems in order to function properly in an optical networking system. The requirements of implementing de-multiplexing and re-multiplexing functions add tremendous complexities to the system configuration and significantly increase the cost of manufacture, system installation, and maintenance of the optical network systems. Another drawback of both of these two types of MEMS-based switches is that these prior art switching systems are not wavelength selective switches. In other words, the switching systems cannot selectively switch a particular wavelength from an input waveguide to a desired output waveguide. In short, they are not wavelength discriminating devices.

In order to have wavelength discrimination, a Bragg grating has been shown to have excellent wavelength selection characteristics. A Bragg grating behaves as a wavelength-selective filter, reflecting a narrow band of wavelengths, while transmitting all other wavelengths. The Massachusetts Institute of Technology (MIT) has developed a technology for building Bragg grating devices in planar optical waveguides. These so-called integrated Bragg gratings offer many advantages over the fiber Bragg grating, according to MIT.

Therefore, a need exists to provide an innovative method for constructing MEMS-actuated highly integrated wavelength selective switches. It is desirable that the improved optical switch be able to eliminate unbalanced power loss, be simple to manufacture, have low insertion loss and power consumption, and be reliable.

Current optical switch systems have serious drawbacks and practical limitations. An example is the optical switch system disclosed in U.S. Pat. No. 6,253,000, in which the building block is a traditional multiport coupler. Drawbacks of this type of switch system include: (1) a large number of couplers are required to scale up the matrix and (2) the insertion loss of signals at various input ports varies greatly. A similar example is described in U.S. Pat. No. 6,208,778. Therefore, a need exists to provide a wavelength intelligent optical switch capable of routing various incoming wavelengths and also capable of scaling up with a relatively simple yet flexible structure. Once fully developed, they will be the building block of various modules used in the optical communication network.

SUMMARY OF THE INVENTION

The present invention discloses methods and apparatus for constructing optical switch systems. These methods and apparatus greatly simplify the structure of large-scale optical switches, compared with known approaches. The methods and apparatus also provide advantages of configuration flexibility, modular construction, constant signal loss, and minimal required numbers of switch units. The optical switch systems are built upon the optical switch modules—another embodiment of this invention. The switch systems comprise M×N switch modules and the switch module in turn comprises a two-dimensional waveguide array and a number of waveguide grating-based wavelength selective switches.

The optical switch module is very flexible in its applications. It can be used as a matrix switch, a de-multiplexer, or a re-multiplexer. With the capability of wavelength-selective routing provided by the switch modules, the optical switch systems disclosed in this invention requires a relatively small amount of switch units to extend into a very-large-scale switch system. The optical switch systems also eliminate unbalanced power loss, simplify the fabrication and packaging processes, reduce the insertion loss and power consumption, and further improve overall reliability. In accordance with the invention, the switch system constructed by the method disclosed performs the de-multiplexing and re-multiplexing functions inherently. Therefore, in one embodiment, no external de-multiplexers and complicated re-multiplexers are needed to form an optical switching functional block. The size and cost of the optical switches are significantly reduced.

BRIEF DESCRIPTIONS OF THE DRAWINGS

The present invention can be better understood with reference to the following drawings. The components within the drawings are not necessarily to scale relative to each other, emphasis instead being placed upon clearly illustrating the principles of the present invention.

DETAILED DESCRIPTION OF THE PREFERRED EMBODIMENT

In the following description, numerous specific details are provided, such as the identification of various system components, to provide a thorough understanding of embodiments of the invention. One skilled in the art will recognize, however, that the invention can be practiced without one or more of the specific details, or with other methods, components, materials, etc. In still other instances, well-known structures, materials, or operations are not shown or described in detail to avoid obscuring aspects of various embodiments of the invention.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more embodiments.

A MEMS-actuated highly integrated wavelength intelligent switch is described in commonly assigned and co-pending U.S. Patent Application Ser. No. 60/338,927 entitled "WAVEGUIDE GRATING-BASED WAVELENGTH SELECTIVE SWITCH ACTUATED BY MICRO-ELECTROMECHANICAL SYSTEM" to Zhang et al., which is incorporated by reference in its entirety herein. The switch is fabricated on a silicon substrate using planar-lightwave-circuit (PLC) and MEMS technologies. The switching action is based on electrostatic bending of a part of waveguide with built-in integrated Bragg gratings. The waveguide with integrated Bragg gratings, referred to as a "Bridge Waveguide", functions as a switching element. When the bridge waveguide is electro-statically bent close enough to an input waveguide, the wavelength, which meets the Bragg phase-matching condition, is coupled into the bridge waveguide. Through the bridge waveguide, the selected wavelength is then directed into a desired output waveguide. With the development of this powerful optical switch unit, a practical optical switch system is feasible. The description below describes an optical system constructed by using this type of optical switch units.

Figure 1A:
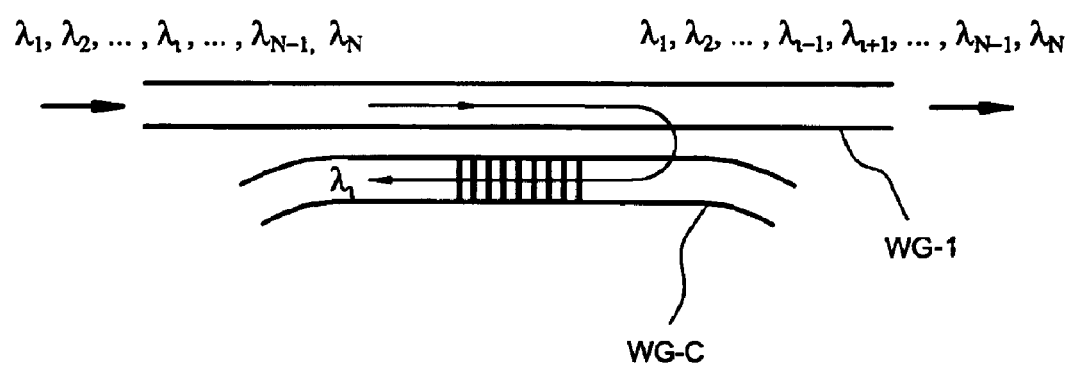
FIG. 1A illustrates the coupling principle of the Bragg grating-based wavelength-selective optical switch, which is used in this invention as a switch unit.

FIG. 1A shows the coupling between a first waveguide WG-1 and a coupling waveguide WG-C. The coupling waveguide has reflective-type Bragg gratings on a portion coupled to the first waveguide WG-1. An optical signal with multiplexed channels represented by wavelengths $\lambda_1$, $\lambda_2$, $\lambda_3$, ..., $\lambda_i$, ..., $\lambda_n$ is transmitted in the first waveguide WG-1. At the coupling portion to a coupling waveguide WG-C with wavelength-selective Bragg gratings, an optical signal of wavelength $\lambda_i$ is reflected to the coupling waveguide WG-C while the remaining portion of the optical signal $\lambda_1$, $\lambda_2$, $\lambda_3$, ..., $\lambda_{i-1}$, $\lambda_{i+1}$, ..., $\lambda_n$ maintains the original transmission path along the first waveguide WG-1.

Figure 1B:
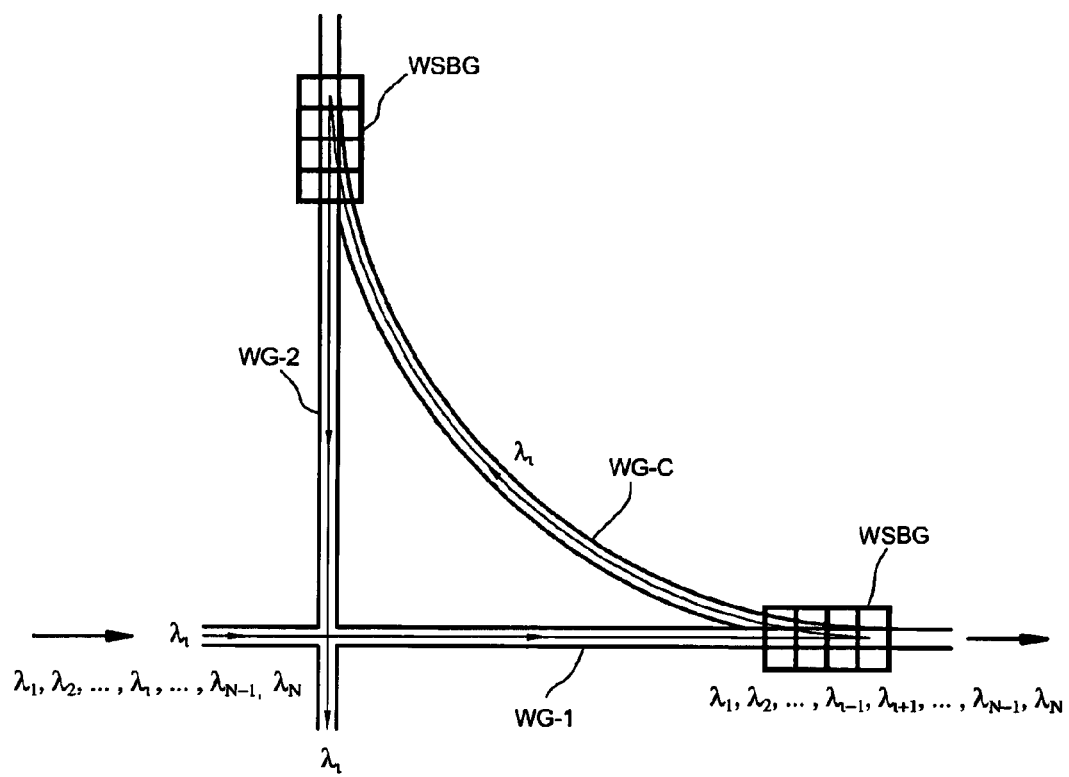
FIG. 1B is a diagram showing the operation and functions of the Bragg grating-based, wavelength-selective optical switch.

FIG. 1B illustrates the operation and function of the optical switch. As shown in FIG. 1B, a multiplexed optical signal is transmitted from WG-1 is wavelength selectively reflected to the coupling waveguide WG-C with an optical transmission of $\lambda_i$. Then, the reflected signal $\lambda_i$ transmitted into the coupling waveguide WG-C is again reflected and transmitted into the second waveguide WG-2. The switching action is based on electrostatically moving WG-C close to or away from WG-1 and WG-2. When the coupling waveguide WG-C is electrostatically bent close enough to WG-1 and WG-2, the wavelength, which meets the Bragg phase-matching condition, is coupled from WG-1 to WG-2. Through WG-C, the selected wavelength is then directed into WG-2.

Figure 2A:
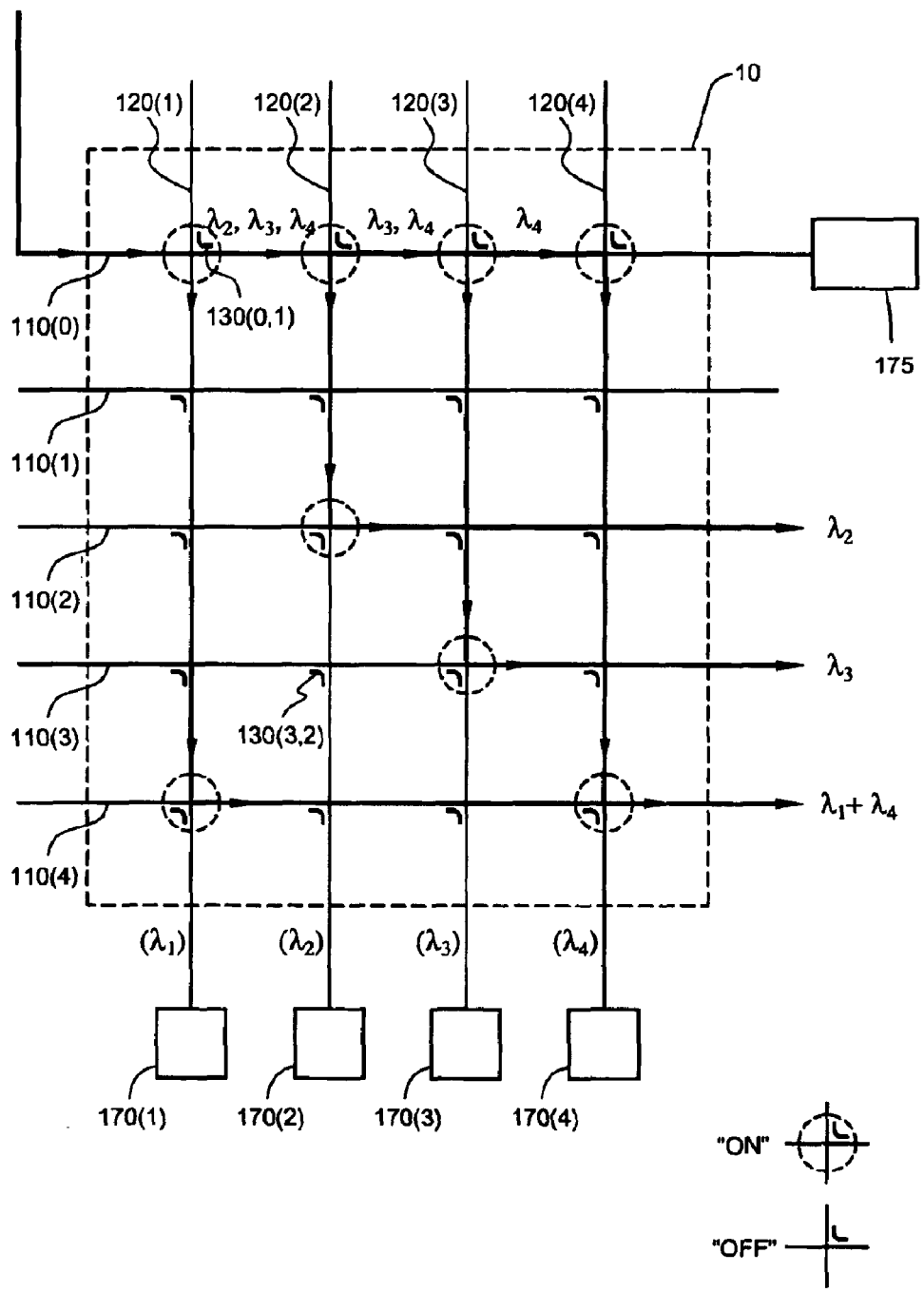
FIGS. 2A and 2B are schematic diagrams of a wavelength selective switch module of this invention.
Figure 2B:
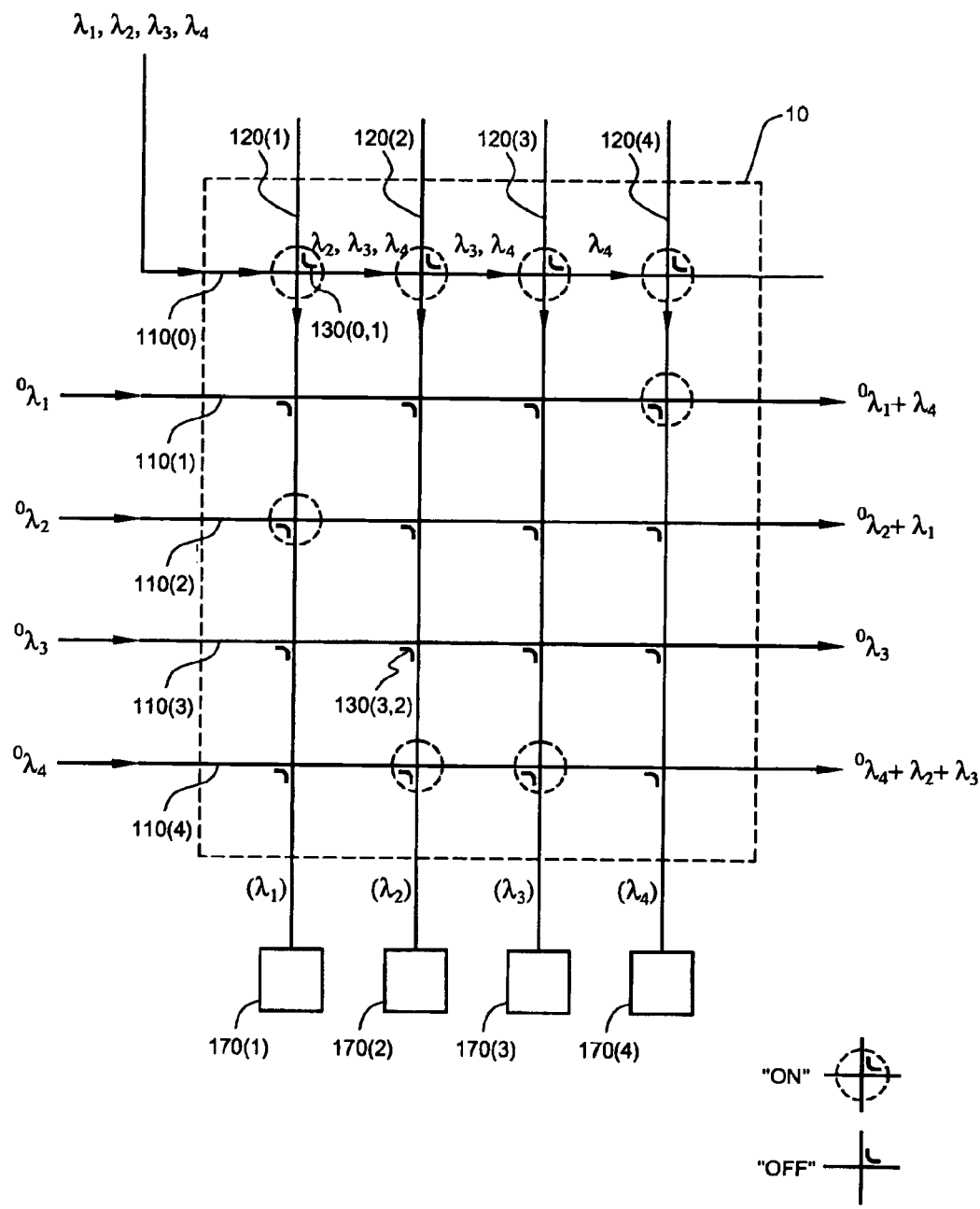

The switch described in FIG. 1B can be fabricated on a silicon substrate using planar-lightwave-circuit (PLC) and MEMS technologies. A plurality of these switch units can be built and integrated on the same substrate. Therefore, a compact optical switch system can be built based on these switches. FIGS. 2A and 2B show simple optical switch systems based on a single optical switch module 10.

FIG. 2A is a schematic diagram for showing the functions of a two-dimensional wavelength selective switching system by using a 4×5 (4 columns and 5 row matrix) optical switch module 10. With four input signals, $\lambda_1, \lambda_2, \lambda_3$, and $\lambda_4$, on the primary input port 110(0) and having four output ports, this system functions as a 4×4 switch. However, it can be appreciated that the switch may be made to any arbitrary size as required by particular system requirements. The optical signal switching module 10 includes a two dimensional array of waveguides shown as horizontal waveguides 110(i) where i=0, 1, 2, 3, and 4 and vertical waveguides 120(j) where j=1, 2, 3, and 4. The horizontal waveguide 110(0) is an input waveguide for receiving an input optical signal that includes four multiplexed wavelengths $\lambda_1, \lambda_2, \lambda_3$, and $\lambda_4$. Advantageously, there is no requirement to de-multiplex (DEMUX) the multiplexed optical signals. The horizontal waveguides 110(i) and the vertical waveguide intersect each other to form a plurality of wavelength selective switching intersections disposed with a wavelength selective grating-based switch 130(i, j) where i=0, 1, 2, 3, and 4, and j=1, 2, 3, and 4. A grating-based switch 130(i, j) is disposed on each of the switching intersections between a horizontal and vertical waveguides 110(j) and 120(j).

Still referring to FIG. 2A, where the input waveguide 110(0) receives a multiple-channel optical signal is represented by $\lambda_1, \lambda_2, \lambda_3$, and $\lambda_4$. The input optical signal is then wavelength selectively switched by a wavelength selective grating switch 130(0, j) to a vertical waveguide 120(j) each transmitting an optical signal of a specific wavelength $\lambda_j$ where j=1, 2, 3, and 4. The wavelength selective grating switches 130(i, j) disposed on the intersections of waveguides 110(i) and 120(j) may be selectively activated. The method and configuration for activating the grating switches will be further described below. The grating switches 130(i, j) are selectively activated to switch optical signals of particular wavelength or combination of wavelengths to output from each of the horizontal waveguides 110(i), where i=1, 2, 3, and 4 implemented as output waveguides. For example, FIG. 2A shows the grating switches 130(4, 1), 130(2, 2) and 130(3, 3) and 130(4, 4) are activated. By activating these grating switches, the output signal on waveguide 110(2) has a signal with wavelength $\lambda_2$. The output signal on waveguide 110(3) has a signal with wavelength $\lambda_3$. The output signal on waveguide 110(4) has a signal with wavelength $\lambda_1$ and $\lambda_4$.

By selectively activating the grating switches 130(i, j), an optical switch operator is provided a large degree of flexibility to alternatively activating different combinations of grating switches to generate output signals of different combination of wavelengths without requiring a re-multiplexing (REMUX) process.

In addition to the flexibility of selectively switching the optical signals of different wavelengths through different combinations of output waveguides, the wavelength-selective optical switch module 10 is further provided with optical ports for connecting to residual signal detectors 170(j), where j=1, 2, 3, 4. An optical port is also provided for connecting to residual input signal detector 175. As shown in FIG. 2A, the residual signal detectors are disposed at the terminations of the vertical waveguides 120(j) and at the termination of input horizontal waveguide 110(0). The residual signal detectors are typically employed for detecting the conditions of operation to determine the functionality of the switching operations and signal levels through the residual signals.

According to above descriptions, this switch system includes an input waveguide designated as waveguide WG(0), e g., 110(0), for receiving a multiplexed optical signal comprising optical signals transmitted over a plurality of wavelength channels represented by $\lambda_1, \lambda_2, \lambda_3, \ldots, \lambda_i, \ldots, \lambda_n$, where N is a positive integer wherein the input waveguide extending over a first direction. The switching system further includes a two dimensional waveguide array comprising a plurality of first direction waveguides WG(i), i=1, 2, 3, ..., M extending over the first direction substantially parallel to the input waveguide WG(0) where M is a positive integer and a plurality of second direction waveguides WG'(j), j=1, 2, 3, ... N, extending over a second direction substantially perpendicular to the first direction and intersecting with the input waveguide and each of the first direction waveguide WG(i), i=0, 1, 2, 3, ..., M, thus forming (M+1)×N intersections. The switching system further includes a plurality of wavelength selective grating switches SW(i, j) where i=0, 1, 2, 3, ... M and j=1, 2, 3, ..., N, each disposed on one of the (M+1)×N intersections for selectively transmitting an optical signal of wavelength $\lambda_j$ into a waveguide WG'(j) and for selectively transmitting an optical signal of a predefined combination of wavelengths into at least one of the waveguide WG(i) for i=1, 2, 3, ... M.

FIG. 2B is a schematic diagram of another optical switch using the same optical switch module 10. The basic configuration and wavelength-selective switching operations of the optical switch module 10 are the same as described in FIG. 2A except that additional optical signals represented by four wavelengths $^0\lambda_1, ^0\lambda_2, ^0\lambda_3$, and $^0\lambda_4$ are input from a corresponding horizontal waveguides 110(j) where j=1, 2, 3, and 4. By turning on or off these switch units, the primary input signals $\lambda_1, \lambda_2, \lambda_3$, and $\lambda_4$ can be switched and combined with those pass-through signals $^0\lambda_1, ^0\lambda_2, ^0\lambda_3$, and $^0\lambda_4$. This simple optical switch system demonstrates the functional flexibility of the optical switch module.

Figure 3A:
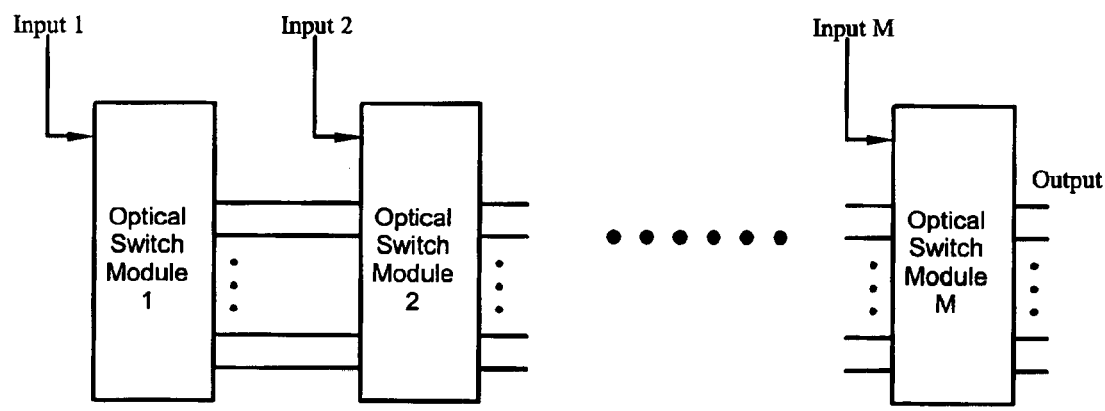
FIGS. 3A and 3B illustrate an arrangement of serial configurations of optical switch systems of this invention.

To scale up the size of the optical switch systems, two or more optical switch modules can be used in a larger optical switch system. An arrangement of constructing a larger optical switch system is shown in FIG. 3A. In this arrangement each output port of a given optical switch module is connected to the pass-through inputs of next optical switch module. This is referred to as a series connection. Each optical switch module shown in FIG. 3A performs similar functions as the optical switch module 10 described in FIGS. 2A and 2B. With this serial-type of connecting, an optical switch system can be expanded easily.

Figure 3B:
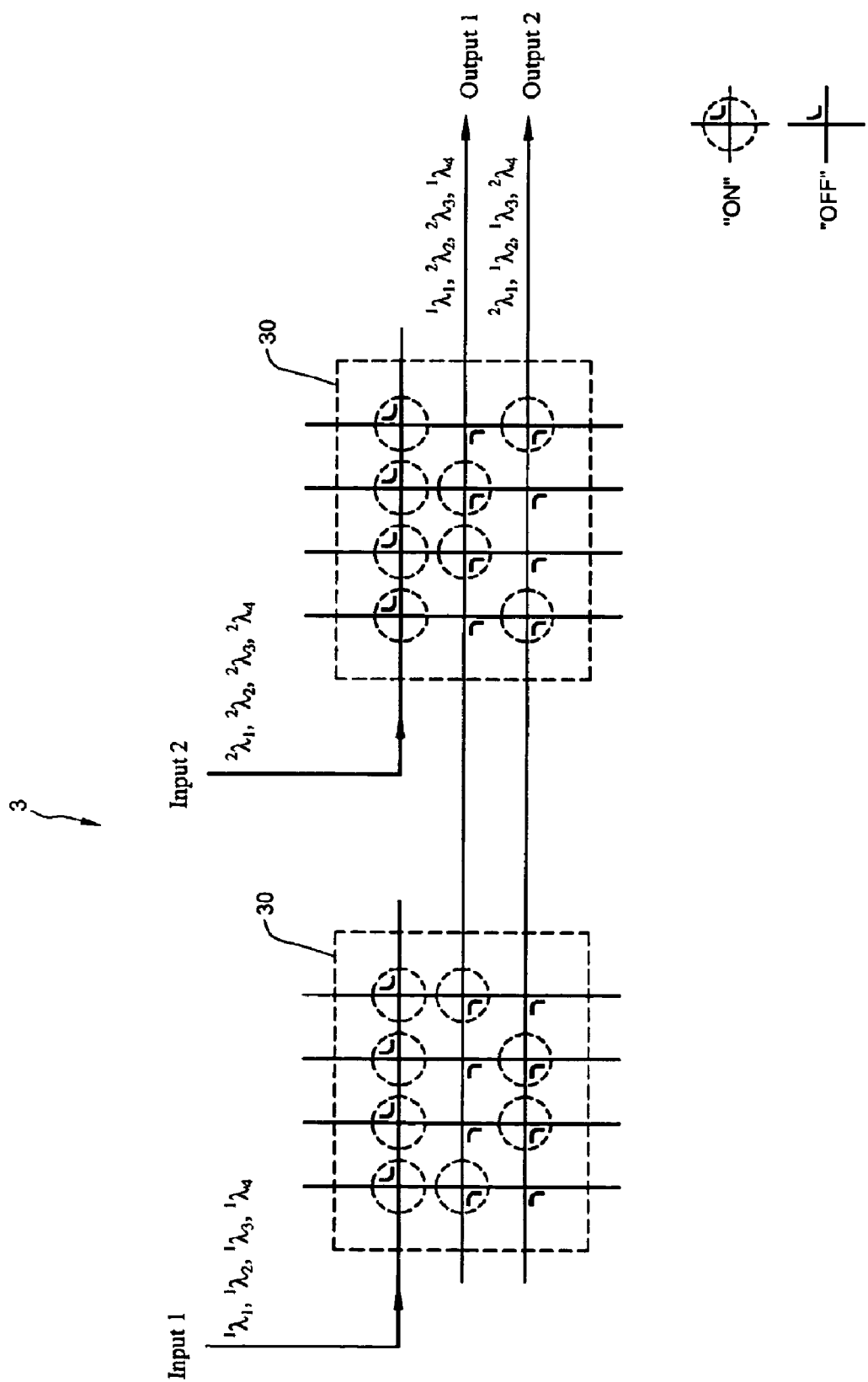

An example of implementation of this arrangement is shown in FIG. 3B. This optical switch system 3 comprises two optical switch modules 30, which function as 4×2 switches. With the ON-OFF setting indicated on FIG. 3B, it can be seen that the input signals $^1\lambda_1$, $^1\lambda_2$, $^1\lambda_3$, and $^1\lambda_4$ on input 1 and $^2\lambda_1$, $^2\lambda_2$, $^2\lambda_3$, and $^2\lambda_4$ on input 2 can be randomly selected and combined into output 1 and output 2. This optical switch system 3 clearly demonstrates the flexibility and simplicity of the arrangement of this invention.

Figure 4A:
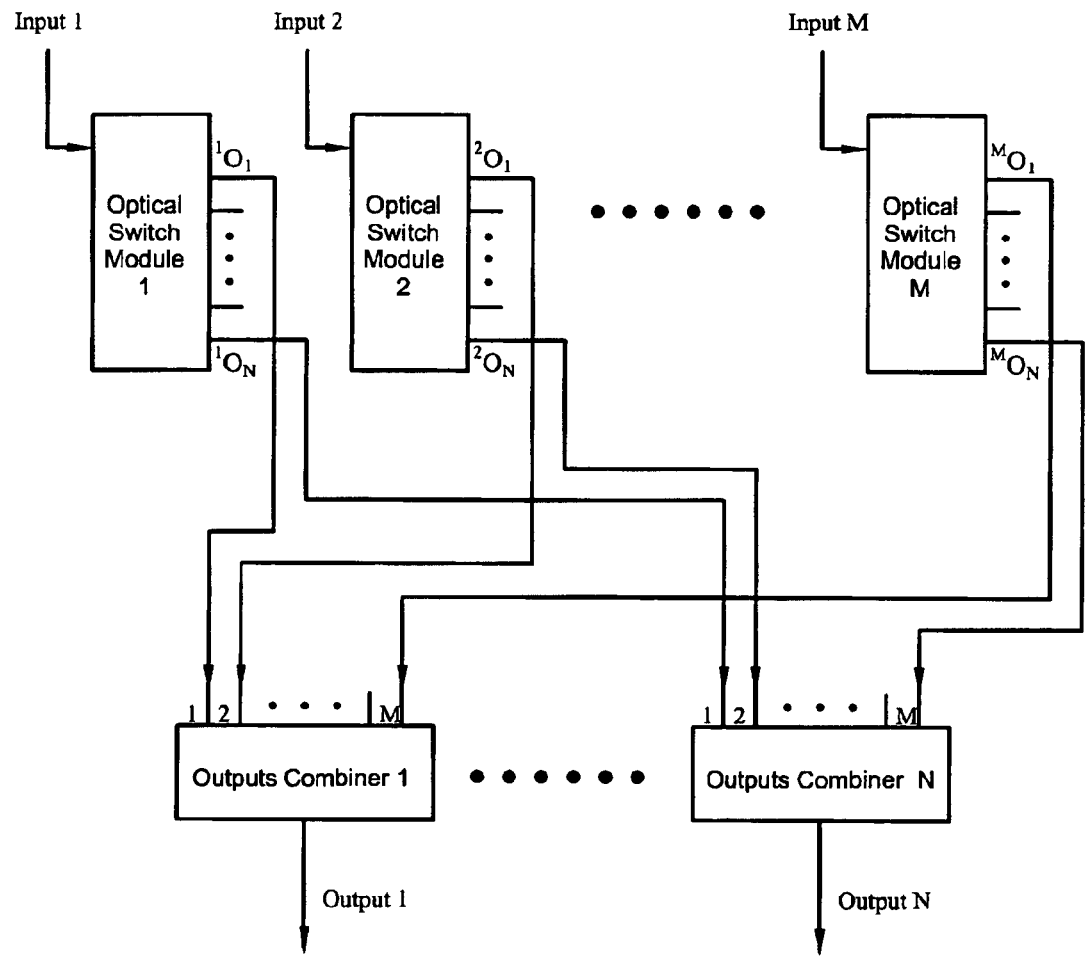
FIGS. 4A, 4B, and 4C illustrate an alterative embodiment of parallel configurations of optical switch systems of this invention.

Another scale-up arrangement of constructing a larger optical switch system is shown in FIG. 4A. This is referred to as a parallel connection. In this arrangement each output port of a given optical switch module is connected to the input ports of a particular output combiner. The arrangement is to connect all the first outputs of all the optical switch modules to Output Combiner 1, all the second outputs of all the optical switch modules to Output Combiner 2, etc. Again, each optical switch module shown in FIG. 4A performs similar functions as the optical switch module 10 described in FIGS. 2A and 2B. The output combiners function as multiplexers and therefore an optical switch module, with proper size, of this invention can be used to perform the function.

Figure 4B:
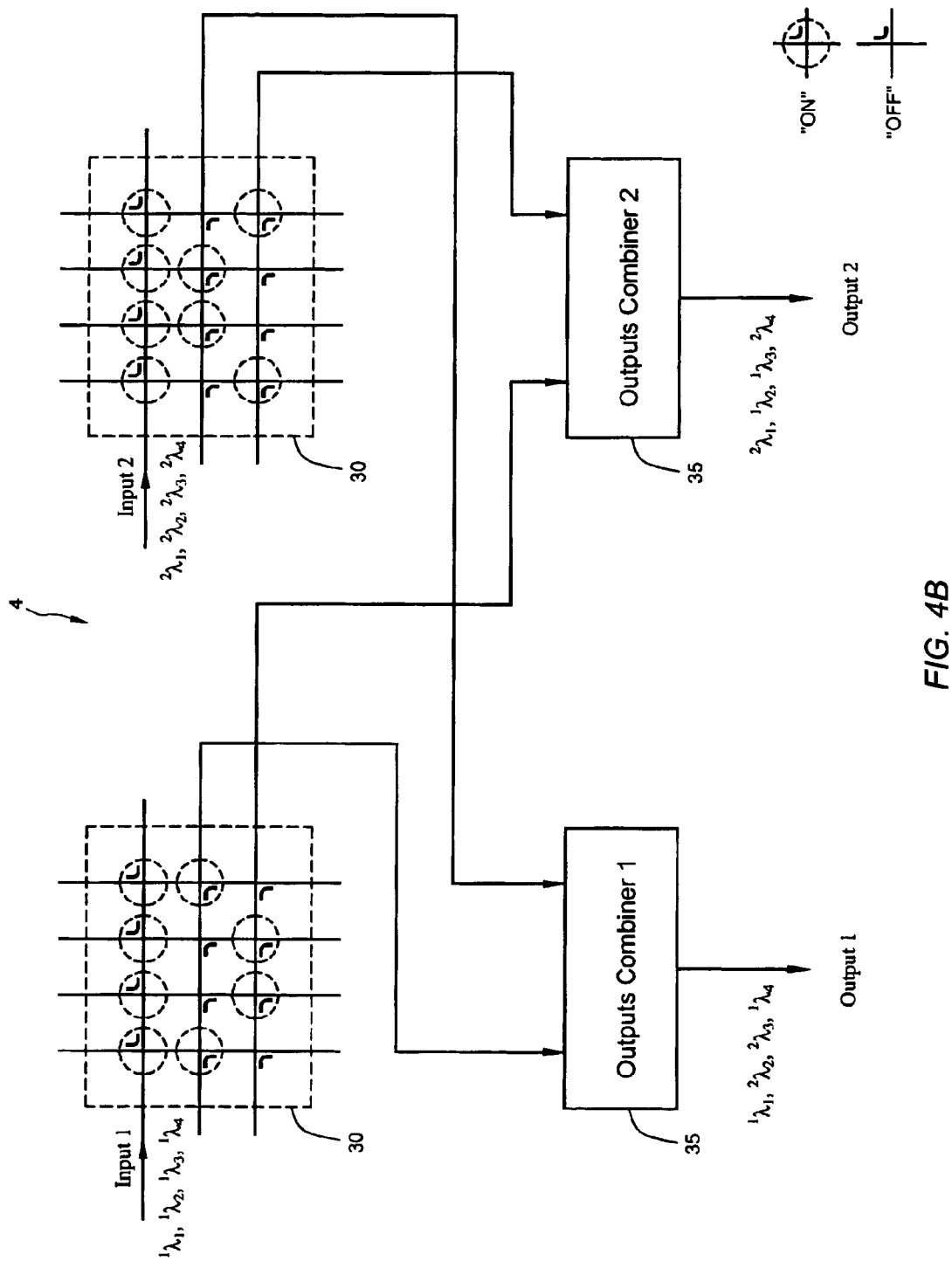

An example of implementation of this arrangement is shown in FIG. 4B. This optical switch system 4 comprises two optical switch modules 30, which function as 4×2 switches and two output combiners 35, which function as multiplexers. With the ON-OFF setting indicated on FIG. 4B, it can be seen that the input signals $^1\lambda_1$, $^1\lambda_2$, $^1\lambda_3$, and $^1\lambda_4$ on input 1 and $^2\lambda_1$, $^2\lambda_2$, $^2\lambda_3$, and $^2\lambda_4$ on input 2 can be randomly selected and combined into output 1 and output 2. The major advantages of this arrangement is that any input signal will pass exactly two "ON" switches of its wavelength and therefore keep the insertion loss of each signal close to identical regardless of the size of the optical switch system. The power loss is also lower because the short optical path for all the input signals.

Figure 4C:
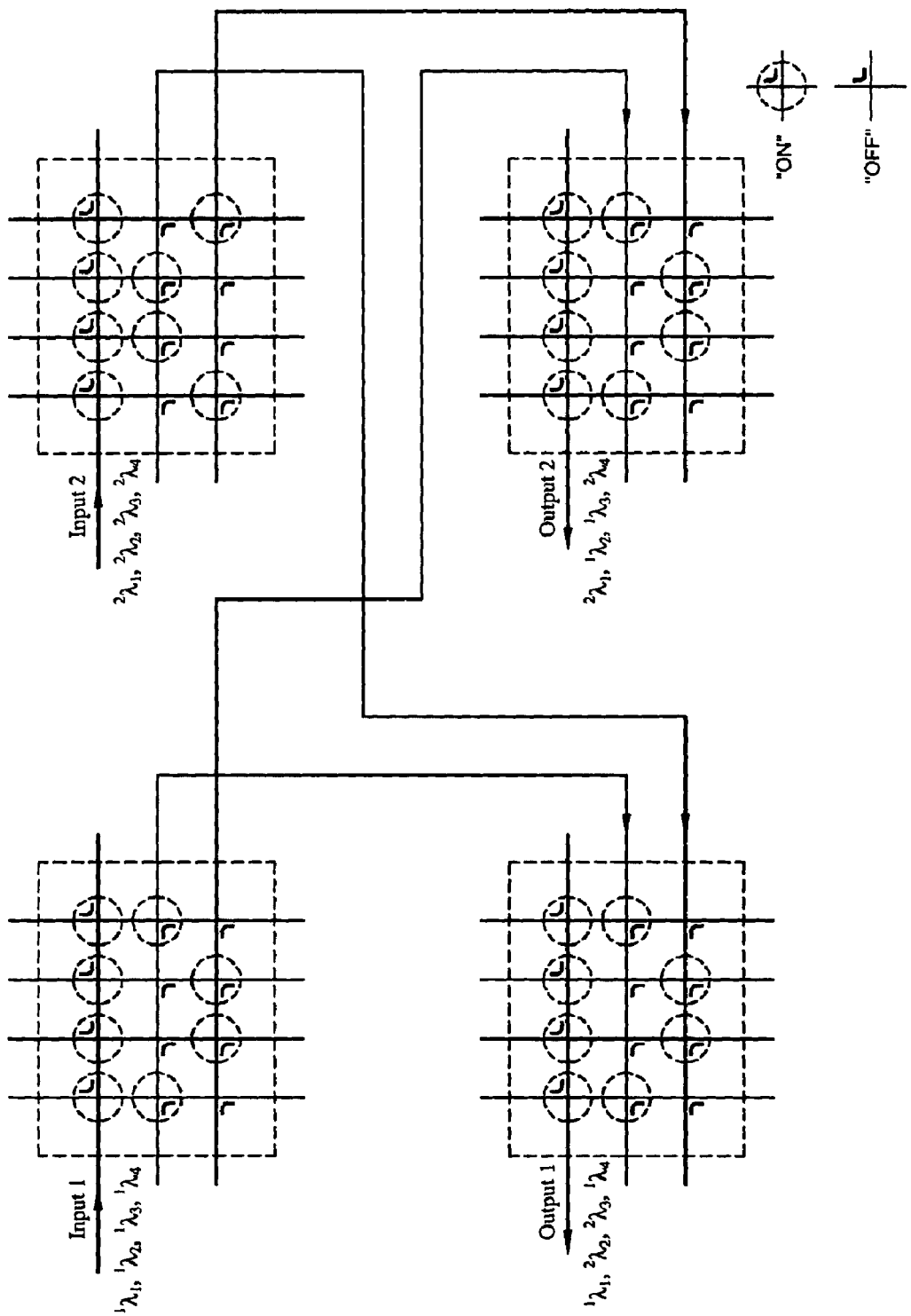

FIG. 4C shows a full implementation of the parallel-type example as described in FIG. 4B. In this implementation the same optical switch modules 30 are used as outputs combiners. This implementation by using only one type of optical switch module demonstrates another advantage of simplicity of fabrication and flexibility of configurations.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

We claim:

1. An optical wavelength-selective switching system comprising: a plurality of optical wavelength-selective switch modules that are connected together, wherein at least two of said wavelength-selective switch modules comprise:

(a) a waveguide array comprising a plurality of first direction waveguides extending over a first direction, one of said plurality of first direction waveguides being an input waveguide carrying an optical signal having a plurality of wavelengths, and a plurality of second direction waveguides intersecting with said input waveguide and at least one of said first direction waveguides to form a plurality of intersections; and (b) a plurality of wavelength-selective grating-based switch disposed on at least one of said plurality of intersections;

wherein said optical wavelength-selective switch modules have at least first and second outputs, said first outputs from said optical wavelength-selective switch modules being routed to an first optical combiner, said second outputs from said optical wavelength-selective switch modules being routed to a second optical combiner, said first and second optical combiners operative to combine the signals from said first outputs and second outputs respectively.

2. The system of claim 1 wherein said wavelength selective grating switch can be engaged or disengaged to said input waveguide and said second direction waveguide.

3. The system of claim 1 wherein said first waveguides and said second waveguides are substantially perpendicular to each other.

4. The system of claim 1 wherein said wavelength-selective switch modules are connected in series.

5. The system of claim 1 wherein said wavelength-selective switch modules are connected in parallel.

* * * * *